(12) United States Patent
Kuchnio et al.

(10) Patent No.: US 10,055,858 B2
(45) Date of Patent: *Aug. 21, 2018

(54) COLOUR CONTRAST ENHANCEMENT OF IMAGES BY NON-LINEAR COLOUR MAPPING

(71) Applicant: SYNAPTIVE MEDICAL (BARBADOS) INC., Bridgetown (BB)

(72) Inventors: Piotr Kuchnio, Burlington (CA); Gal Sela, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

This patent is subject to a terminal disclaimer.

(21) Appl. No.: 15/797,399

(22) Filed: Oct. 30, 2017

(65) Prior Publication Data

US 2018/0047187 A1 Feb. 15, 2018

Related U.S. Application Data

(63) Continuation of application No. 15/108,491, filed as application No. PCT/CA2015/050841 on Sep. 2, 2015, now Pat. No. 9,824,466.

(51) Int. Cl.
*G06T 11/00* (2006.01)
*G06T 5/40* (2006.01)
*G06T 7/90* (2017.01)

(52) U.S. Cl.
CPC .............. *G06T 11/001* (2013.01); *G06T 5/40* (2013.01); *G06T 7/90* (2017.01)

(58) Field of Classification Search
CPC ..... G06T 19/20; H04N 1/6027; H04N 1/6058
See application file for complete search history.

(56) References Cited

U.S. PATENT DOCUMENTS

| | | | |
|---|---|---|---|
| 5,796,873 A * | 8/1998 | Deane ................. | H04N 1/4092 358/532 |
| 7,755,817 B2 | 7/2010 | Ho et al. | |
| 2009/0204913 A1 | 8/2009 | Kawano et al. | |
| 2012/0293814 A1* | 11/2012 | Namikata ............ | H04N 1/6058 358/1.9 |
| 2013/0201206 A1* | 8/2013 | Bryant .................. | H04N 1/407 345/600 |
| 2013/0236067 A1 | 9/2013 | Cherna et al. | |

(Continued)

FOREIGN PATENT DOCUMENTS

WO 2015026874 A1 2/2015

*Primary Examiner* — Edward Park
(74) *Attorney, Agent, or Firm* — Kagan Binder, PLLC (57) ABSTRACT

An image enhancement system and method for enhancing medical images from a surgical imaging system. Each image pixel has a value in a first three-dimensional color space. A mapping of values in a subset of the first color space is calculated to map each color point in the subset to an enhanced value. The mapping is calculated by selecting a reference point in the subset and, for each color point in the subset, mapping the color point to a modified color value offset from the reference point by the modified color point vector that has the same direction as the color point vector extending from the reference point to the color point, but a greater magnitude. The mapping is applied to the pixel values in the medical image falling in the subset to produce an enhanced image.

20 Claims, 3 Drawing Sheets

(56) References Cited

U.S. PATENT DOCUMENTS

2016/0088194 A1* 3/2016 Schutte ................ H04N 1/6077
382/167
2016/0217575 A1* 7/2016 Bernal .................... G06T 7/408

\* cited by examiner

COLOUR CONTRAST ENHANCEMENT OF IMAGES BY NON-LINEAR COLOUR MAPPING

PRIORITY CLAIM

This application is a continuation application of U.S. Ser. No. 15/108,491, filed Jun. 27, 2016, which claims benefit from International Application No. PCT/CA2015/050841, filed Sep. 2, 2015, all of which are incorporated herein by reference in their entireties for all purposes.

FIELD OF THE INVENTION

The present invention relates generally to systems and methods for colour contrast enhancement of medical images, and more particularly to colour contrast enhancement of medical images where the contrast enhancement spreads the colour values in a specified subset of a colour space.

BACKGROUND OF THE INVENTION

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stern cell delivery, adaptive chemotherapy regimes, surgical tumour resection and radiation therapy are only a few examples of procedures utilizing imaging guidance in the medical field.

Real-time imagery of tissue being operated on may be generated by a surgical imaging system. Typically this is a sequence of images forming a video stream that is updated as a surgical operation is performed. Often there is a particular feature in the imagery that is the subject of the operation such as a glioma, white matter tracts, tendons, ligaments or muscle fibers. It may be very important for the surgeon to be able to distinguish different portions of the feature and distinguish the feature from surrounding tissue. However, while the feature may have distinguishing colour characteristics in colour imagery, it may be difficult for the surgeon to see such distinctions in a typical image or video stream.

In particular, in neurosurgery, tumours and other objects of interest often have poor colour differentiation from their surroundings. For example, a glioma can appear as a slightly off-white region in white matter. The same is true for white matter tracts in brain tissue. The ability to differentiate cancerous tissue from surrounding healthy tissue, or to find other areas of interest, is key for positive outcomes during surgery. Many of the hundreds of clinical decisions made during surgery rely on the surgeon's ability o differentiate anatomy based on contrast.

SUMMARY OF THE INVENTION

In various examples, the present disclosure provides an image enhancement system for enhancing medical images. The system includes a non-transitory computer-readable memory, an electronic interface, and a computer processor. The computer processor is configured to receive and process via the electronic interface, from a surgical imaging system, and store in the computer-readable memory, a medical image, or a sequence of medical images. Each medical image contains a number of pixels, each pixel having a value in a first three-dimensional colour space. The first colour space is preferably the (Cartesian) RGB colour space. The processor is further configured to receive a mapping of values in a subset of the first colour space. The mapping specifies a modified colour value for each colour point in the subset. The mapping is calculated by selecting a reference point in the subset and, for each colour point in the subset, mapping the colour point to the modified colour value offset from the reference point by a modified colour point vector. Each modified colour point vector is calculated based on the colour point vector extending from the reference point to the colour point, each colour point vector having a direction and a magnitude. The processor is further configured to apply the mapping to the pixel values in the medical image falling in the subset to produce an enhanced image.

The modified colour point vector for each colour point in the subset preferably has a direction equal to the direction of the colour point vector of the colour point, and a magnitude greater than the magnitude of the colour point vector. The modified colour point vector may be calculated by adding to the colour point vector a vector in the direction of the colour point vector having a magnitude equal to a constant with a value greater than zero. Alternatively, the modified colour point vector may be calculated by adding to the colour point vector a vector in the direction of the colour point vector having a magnitude equal to a contrast enhancement value that is a non-negative monotonically decreasing function of the magnitude of the colour point vector.

The subset of the first colour space may be convex and the reference point may be selected to be the geometric centre of the subset. The first colour space may be the RGB colour space, and the subset of the first colour space may be a cuboid subset of the RGB colour space. The subset of the first colour space may be the subset of the first colour space corresponding to a subset of a second color space specified by upper and lower bounds of each of the three dimensions in the second colour space. In such cases, the first colour space may be the RGB colour space and the second colour space may be the HSV colour space. Other colour spaces such as YCbCr and CIELAB may alternatively be used. The image enhancement system may also include a display device for displaying images to a user, and a user input device for receiving input from a user. Then the user may specify the upper and lower bounds of the colour space dimensions via the user interface, and the computer processor may receive the specification of the upper and lower bounds from the user interface, and display to the user on the display device the enhanced image.

The computer processor may be further configured to automatically determine the upper and lower bounds by analysis of a specified portion of the medical image. The specified portion of the medical image may contain a glioma.

The computer processor may be further configured to repeatedly enhance image frames of a video stream provided by a surgical imaging system in real-time and display the sequence of enhanced images on a display device.

The invention also provides a method of enhancing a medical image performed by a computer processor. The computer processor first receives from a surgical imaging system a medical image formed of pixels. Each pixel has a value in a first three-dimensional colour space. The computer processor receives a mapping of values in a subset of the first colour space. The mapping specifies a modified colour value for each colour point in the subset. The mapping is calculated by selecting a reference point in the subset and, for each colour point in the subset, mapping the colour point to the modified colour value offset from the reference point by a modified colour point vector calculated based on the colour point vector extending from the reference point to the colour point. The colour point vectors each have a direction and a magnitude. The computer processor then applies the mapping to the pixel values in the medical image falling in the subset to produce an enhanced image.

In this method, for each colour point in the subset, the modified colour point vector may have a direction equal to the direction of the colour point vector of the colour point, and a magnitude greater than the magnitude of the colour point vector.

The method may further include a step of calculating the mapping of values in the subset of the first colour space. This may be done by first selecting the reference point in the subset, and then processing each colour point in the subset of the first colour space. For each colour point, a colour point vector extending from the reference point to the colour point is calculated. For each colour point, a modified colour point vector having a direction equal to the direction of the colour point vector, and a magnitude greater than the magnitude of the colour point vector is calculated. Then, the colour point is mapped to the modified colour value offset from the reference point by the modified colour point vector.

In this method, preferably the subset of the first colour space is convex and the reference point is selected to be the geometric centre of the subset. The first colour space may be the RGB colour space, and the subset of the first colour space may be specified by specifying upper and lower bounds in each of the three dimensions in a second colour space. The second colour space may be the HSV colour space so that the upper and lower bounds define a subset of the HSV colour space corresponding to a cuboid subset of the RGB colour space.

The method may further include a step of providing a user interface to a user to permit the user to specify the upper and lower bounds, and displaying to the user the medical image showing only the pixels with values in the subset of the HSV colour space defined by the upper and lower bounds.

The method may further include a step of providing a user interface to a user to permit the user to specify the upper and lower bounds, and displaying to the user the enhanced image produced based on the subset defined by the upper and lower bounds.

DETAILED DESCRIPTION OF THE INVENTION

Figure 4:
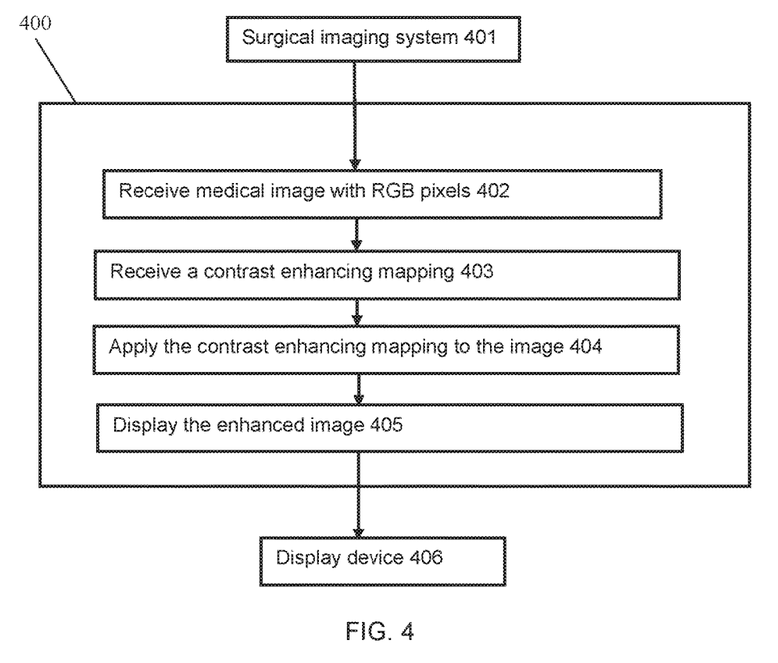
FIG. 4 shows the main steps in the processing of images provided by a surgical imaging system.

The invention is a system and method for increasing colour contrast in particular portions of the colour space of an image or of a video stream. The colour contrast enhancement algorithm boosts perceived contrast for clinically relevant colours. This may be performed in real-time on a surgical camera video feed or more generally on images received from a surgical imaging system 401 (FIG. 4). For example, with the algorithm applied to enhance the imagery, a glioma that would ordinarily appear largely indistinguishable from the background may appear as a highly contrasted region in otherwise healthy white matter. This is accomplished by mapping the pixel values within a particular portion of the colour space in the images received from the camera to new values where they are spread further apart.

The term "colour space" as used herein refers to a particular coordinate representation of points in an RGB colour model. The term "RGB colour space" as used herein means the Cartesian (cube) representation of an RGB colour model having orthogonal red, green and blue axes.

A digital colour image is composed of pixels that are values in a three dimensional colour space. For example, values provided by a camera for each pixel are typically represented by three numbers, such as three 8, 12 or 16 bit digital values, corresponding to the intensities of red, green and blue in what will be referred to as the RGB colour space. The RGB colour space is widely employed for video equipment, such as cameras and displays.

A feature in a medical image, such as a glioma, may be distinguishable from other tissue by its colour. The system receives an image or a sequence of images from a surgical imaging system. Each image, or frame of video, is a colour image being a rectangular array of pixels in a particular colour space. For example, each image may be a rectangular array of 1920 by 1080 pixels, where each pixel is a 24-bit value, eight bits specifying the intensity of the red channel, eight bits specifying the intensity of the green channel and eight bits specifying the intensity of the blue channel.

The system receives 403 a specification of a portion (a subset) of the colour space in which a feature of interest is known or thought to reside. This can be any subset of the three dimensional colour space, although it is generally one or more convex subsets, each of which is often a cuboid or a rectangular cuboid of a colour space. It is generally preferable to specify such subsets in a second colour space such as HSV (hue, saturation and value) or HSL (hue saturation and level), particularly where a human is specifying the subset. Other colour spaces, such as YCbCr, Y'CbCr, Y Pb/Cb Pr/Cr, XYZ, or CIELAB may alternatively be employed. It is generally not preferred to specify the subset directly in the RGB colour space. HSL and HSV are the two most common cylindrical-coordinate representations of points in an RGB color model. These spaces are more intuitive and perceptually relevant than the Cartesian (cube) representation of an RGB colour model. It is generally straight forward to transform pixel values from a first colour space to a second colour space, each representing points in a common colour model. This is typically done using a 3×3 colour transformation matrix with an optional offset vector. This colour transformation can be pre-calculated and then applied to a sequence of video images, for example.

The system may present to the user a user interface that allows the user to specify lower and upper bounds for each of the three colour dimensions, such as hue, saturation and value. At the same time, the system may display to the user an image, or multiple images, that contains a feature of interest, such as a glioma. The user interface may employ two slider controls to set lower and upper bounds for each dimension, and when the user moves a slider, thereby specifying a subset of the colour space consisting of the cuboid subset of that colour space defined by the three upper and lower bounds, then the system may, for example, display in a window only the pixels in an image containing the feature(s) of interest that fall within the specified subset, optionally beside an unedited version of the image. The user may then vary the upper and lower bounds, and the system update the display, to ensure that all points of interest are included in the subset. Alternatively or additionally, the system may display an enhanced image with the contrast in the specified subset enhanced as described below.

The user interface may permit the user to select and cycle though multiple 3D look-up tables (LUTs). For example, the LUTs may be defined on the basis of the pathology/tumour. For example the user may be able to cycle through a red enhance, a blood suppress, a glioma enhance, etc., until the user finds a mapping that the user is happy with.

In some embodiments, the system may automatically determine the upper and lower bounds by analysis of a specified portion of a medical image. For example, a user may specify a portion of the image, for example using a bounding rectangle that contains a glioma. Then the system may analyze that portion of the image and determine a candidate subset of the colour space based on the three dimensional histogram of the specified portion. In some embodiments, the system may automatically segment a feature, such as a glioma, in the specified portion and select the subset to be a subset including most or all of colour values of the pixels in the segmented feature. The system may display the results to the user and allow the user to fine tune the specification of the subset of the colour space.

Figure 2:
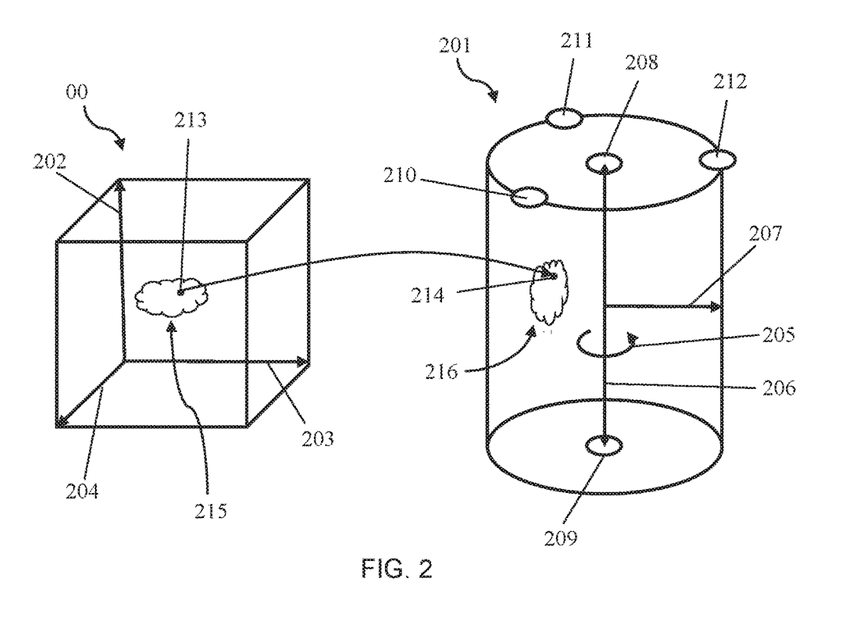
FIG. 2 depicts the correspondence of RGB colour space with HSV colour space.

FIG. 2 depicts a Cartesian RGB colour space 200 on the left, and an HSV colour space 201 on the right. The RGB space 200 has red 203, green 202 and blue 204 orthogonal axes. The HSV space 201 employs cylindrical coordinates, the three dimensions being hue 205, saturation 207 and value 206. Points corresponding to black 209, white 208, red 212, green 211 and blue 210 are indicated in FIG. 2. An arbitrary subset of the HSV space is indicated as item 216, which corresponds to the subset 215 of the RGB space. Values in one space can be mapped to equivalent values in the other space by well-known methods, for example using a 3D LUT. For example, FIG. 2 shows point 213 in RGB space 200 in the subset 215 of the RGB space being mapped to the corresponding point 214 in the subset 216 of the HSV space 201.

Figure 3:
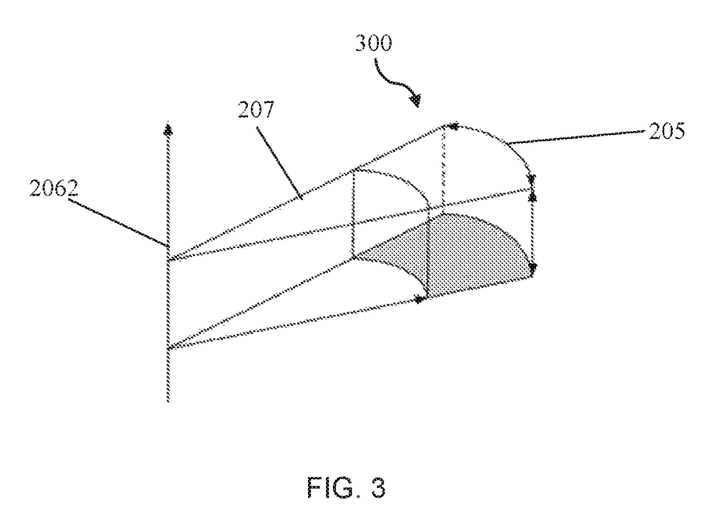
FIG. 3 depicts a subset of HSV colour space that has been selected.

The specified subset of the second colour space, being HSV space in FIG. 2, may be specified by lower and upper bounds on the three colour dimensions, resulting in a subset such as the subset 300 depicted in FIG. 3. Such subsets generally map to quadrilaterally faced hexahedrons or "cuboids" in RGB space, which are convex and have a well-defined centre point.

Two points (a start point and an end point) in a colour space define a vector having a magnitude equal to the distance between the two points and a direction from the start point to the end point. For example, in FIG. 1, start point 101 and end point 103 define the vector 102, and start point 101 and end point 105 define the vector 104. If the start point is a reference point having coordinates $(R_0, G_0, B_0)$ and an end point has coordinates $(R_i, G_i, B_i)$, then the magnitude of the vector from the reference point to the end point may be defined as the square root of the sum: $(R_i-R_0)^2+(G_i-G_0)^2+(B_i-B_0)^2$. Other metrics may alternatively be used.

Once the subset has been specified, then a reference point in the subset in RGB space must be selected. This is generally preferred to be the geometric centre of the subset in RGB space, such as the point 101 of the subset 100 of RGB colour space depicted in FIG. 1. It is preferred that the reference point is selected so that the vector from the reference point to any other point in the subset is contained entirely within the subset. This is of course the case where the subset is a cuboid and the reference point is the centre of the cuboid. Given the reference point, the colour point vector for each colour point in the subset is defined to be the vector with start point being the reference point and end point being the colour point. Each such colour point vector has a direction and a magnitude, with the exception of the reference point, whose colour point vector is the null vector with a magnitude of zero.

Figure 1:
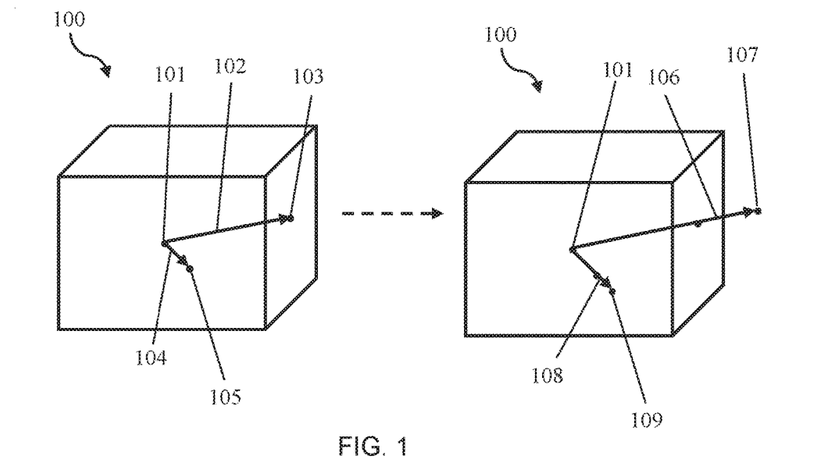
FIG. 1 depicts points in a subset of RGB colour space being mapped to modified colour values.

In preferred embodiments, a mapping between points in the RGB colour space is defined so that each colour point 103, 105 in the subset is mapped to a modified colour value 107, 109 offset from the reference point 101 by a modified colour point vector 106, 108 calculated based on the colour point vector 102, 104 extending from the reference point 101 to the colour point 103, 105. In some preferred embodiments, the mapping is defined as:

$$Pi'=(Pi+\text{Vcorr}*\alpha)T^\gamma.$$

Pi is the colour point $(R_i, G_i, B_i)$, and Vcorr is a normalized colour point vector with start point being the reference point, $P_0$, and end point Pi. T is an optional linear colour correction matrix. It may be desirable to, for example, increase the amount of red in the image, which can be done via T. Of course T may be set to the identity matrix in some embodiments. The normalized colour point vector is the same as the colour point vector except that the coordinate values have been scaled (by dividing by the magnitude of the colour point vector) so that the normalized colour point vector has a magnitude equal to one. $\alpha$ is a contrast enhancement value that is preferably a real-valued number that is greater than zero. The calculation of Pi' may also incorporate a gamma correction using a gamma factor ($\gamma$), which is a well-known non-linear luminance mapping technique, following a power law. As gamma is increased, the image becomes darker. When gamma is decreased, the image becomes lighter.

FIG. 1 depicts the mapping of two points 103, 105 in the RGB colour space subset 100 to two modified colour values 107, 109. For point 103, the correction, Vcorr*$\alpha$ is shown as an incremental vector 106, and for point 105 as vector 108.

For uniform enhancement, $\alpha$ is a constant. In some cases it may be desirable, for example, to spread colours closer to the centre of the cluster more aggressively than those at the edge of the cluster, in which case $\alpha$ may be a function of the distance from the reference point to the colour point, such as:

$$\alpha = \alpha'\left(1 - g\frac{d_i}{d_{max}}\right).$$

In the above, $\alpha'$ is a constant greater than zero, $d_i$ is the distance from the reference point to Pi (i.e. the magnitude of the colour point vector for Pi), $d_{max}$ is the maximum distance of any point in the subset from the reference point, and g is a gain factor that is preferably greater than zero and less than or equal to one. If g is set to one, then the colour point in the subset furthest from the reference point would be unchanged by the mapping (although its separation from other points in the subset closer to the reference point would still be increased). More generally, $\alpha$ may be defined to be any monotonically decreasing function of the magnitude of the colour point vector.

Of course, while it is preferred, it is not essential that the reference point be the geometric centre point of the subset.

For example, a user may specify a desired reference point based on the user's knowledge of the feature that is seen in an image. In other embodiments, the reference point may be selected to be the colour value of the subset occurring most often in an image.

Similarly it is not essential that α be greater than zero. In some applications, having α be negative so that the selected subset of the colour space is contracted may be beneficial, but this is not generally preferred.

FIG. 4 depicts the operation of an example image enhancement system 400 that is receiving 402 medical images with RGB pixels from a surgical imaging system 401, and in real-time is enhancing each image or image frame and displaying the enhanced images 405 on a display device 406. Typically the surgical image system 401 is imaging a portion of a. patient's body that a surgeon is operating on and the display device 406 is positioned so that the surgeon can view the enhanced images displayed on the display device 406 as the surgeon operates, with changes to the portion of the patient's body being imaged being reflected in the enhanced imagery shown on the display device 406 in real time. The system receives a contrast enhancing mapping 403, calculated as described herein. The same system 400 may also calculate the mapping, typically as a 3D LUT, and/or modify the mapping during surgery, but typically the mapping is calculated before starting the surgery. As each image or image frame is received, the system applies the mapping to each image 404 to produce enhanced images.

Preferably the contrast enhancing mapping is pre-calculated and stored as a 3D LUT before the surgical procedure starts. Many such 3D LUIS may be pre-calculated to work well with particular features, such as glioma, white matter tracts, flesh tones, blood tone enhancement and muscle fibres. Multiple mappings may be produced for use with a single feature, and the surgeon may be given the option to switch between them in real-time during surgery. In some embodiments though, the mapping may be calculated and/or adjusted on the fly during surgery. For example, a surgeon may have removed most of a feature but some portions of the feature may remain that were not optimally enhanced with the pre-calculated mapping. In such a case, the surgeon may, for example, be able to select a different subset of the colour space and the system then calculates and applies a new mapping.

It will be noted that the algorithm described herein is inherently non-linear in nature. The use of a 3D LUT to map pixel vales is a very computationally efficient method of implementing such non-linear mappings.

In some embodiments, the mapping may be dynamically calculated by the system 400 so that, for example, the surgeon can vary the value of the contrast enhancement value, a, either directly, or, for example, by varying a gain factor g, as discussed above. In some embodiments, the surgeon may also be able to vary the subset of the colour space in real-time and immediately see the results of the modified mapping as the subset is varied (for example using three sliders, one for each colour dimension in HSV space).

It will be noted that the colour mapping as described herein will in some cases result in some colour points, such as point 103 in FIG. 1, being mapped to colour values, such as point 107, that lie outside the selected subset of the colour space. The mapping may expand the subset to an expanded subset of the colour space. In such cases, there will be some image pixels that were initially outside the subset but which fall in the expanded subset. Such pixels are not mapped by the mapping described above, and so will overlap in colour with pixels in the subset after the enhancement unless they are also mapped. In many cases this will not cause undesirable results. However, in some cases, it will be preferable to extend the colour mapping so that it includes colour points outside of the subset to cause them to be mapped to points falling outside the expanded subset. Various methods of doing this may be used, For example, a simple approach would simply map each point originally outside the subset that is within the expanded subset to the point in the direction of its colour point vector on the boundary of the expanded subset. More sophisticated methods that maintain colour separation between points outside of the subset may alternatively be used.

The above description generally assumes that the specified subset of the colour space is a single connected subset, typically being convex, and generally cuboid in RGB space. However, the methods described herein are readily used with subsets of the colour space that are the union of a number of connected subsets where each connected subset does not overlap any of the other connected subsets. In such embodiments, the same approach as described above is used on each connected subset in turn. For example, a separate reference point, typically the geometric centre, would be selected in each connected subset, and each point in a connected subset would be enhanced based on the colour point vector extending from the centre of that connected subset to the colour point.

In further embodiments, the colour enhancement system 400 in FIG. 4 may be used to create and output pathology data whereby the results may be configured as an input into an informatics system for further analysis. Methods of integration of pathology data into an informatics system are further elaborated in international application WO/2014/139021—"INTRAMODAL SYNCHRONIZATION OF SURGICAL DATA", wherein the application is incorporated by reference herein.

In further embodiments, the methods described herein may be used to re-map a particular illuminator to look like another one. For example, an LED light source can be mapped to look like a Xenon light source. The algorithm could also be used to map the appearance of one camera to another camera. For example a camera's colour appearance can be mapped to the appearance of a KARL STORZ or Stryker camera. Such mappings may be advantageous since some surgeons find the "warm" appearance of Xenon more pleasing than LED. Also, some users prefer (or are used to) the characteristic appearance of the images that come from certain vendors. The described methods and systems can reproduce the appearance of a particular camera. For example, the system may incorporate a "Storz" setting on the camera so that the appearance of a KARL STORZ camera is reproduced when that setting is employed.

In further embodiments, the methods described herein may be used to map information from a number of independent, spatially aligned sources. For example, in magnetic resonance imaging there may be a variety of scan protocols tuned to different contrast mechanisms (e.g. T1, T2, Proton Density scans). It is often impossible to differentiate a lesion in just one scan, but combining information from multiple scans can often improve the ability of a surgeon to identify a likely lesion. Essentially the same thing can be done optically. Each pixel in an image of a portion of a patient can be measured by a variety of sensors and the value of that pixel in the output image may then be determined by a non-linear combination of all the input values of that pixel.

One example of how this is done is through a "k-nearest neighbor" (knn) algorithm to map a variety of input values to a particular labelling.

Generally, a computer, computer system, computing device, client or server, as will be well understood by a person skilled in the art, includes one or more than one computer processor, and may include separate memory, and one or more input and/or output (I/O) devices (or peripherals) that are in electronic communication with the one or more processor(s). The electronic communication may be facilitated by, for example, one or more busses, or other wired or wireless connections. In the case of multiple processors, the processors may be tightly coupled, e.g. by high-speed busses, or loosely coupled, e.g. by being connected by a wide-area network.

A computer processor, or just "processor", is a hardware device for performing digital computations. A programmable processor is adapted to execute software, which is typically stored in a computer-readable memory. Processors are generally semiconductor based microprocessors, in the form of microchips or chip sets. Processors may alternatively be completely implemented in hardware, with hard-wired functionality, or in a hybrid device, such as field-programmable gate arrays or programmable logic arrays. Processors may be general-purpose or special-purpose off-the-shelf commercial products, or customized application-specific integrated circuits (ASICs). Unless otherwise stated, or required in the context, any reference to software running on a programmable processor shall be understood to include purpose-built hardware that implements all the stated software functions completely in hardware.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as ROM, volatile RAM, non-volatile memory, cache or a remote storage device.

A non-transitory computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. For example, all the described processing functions may be implemented in software that runs on one or more programmable processors. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In any case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Where, in this document, a list of one or more items is prefaced by the expression "such as" or "including", is followed by the abbreviation "etc.", or is prefaced or followed by the expression "for example", or "e.g.", this is done to expressly convey and emphasize that the list is not exhaustive, irrespective of the length of the list. The absence of such an expression, or another similar expression, is in no way intended to imply that a list is exhaustive. Unless otherwise expressly stated or clearly implied, such lists shall be read to include all comparable or equivalent variations of the listed item(s), and alternatives to the item(s), in the list that a skilled person would understand would be suitable for the purpose that the one or more items are listed.

The words "comprises" and "comprising", when used in this specification and the claims, are to used to specify the presence of stated features, elements, integers, steps or components, and do not preclude, nor imply the necessity for, the presence or addition of one or more other features, elements, integers, steps, components or groups thereof.

What is claimed is:

1. An image enhancement system for enhancing digital images, the system comprising:
   (a) a non-transitory computer-readable memory;
   (b) an electronic interface; and
   (c) a computer processor configured to:
      (i) receive, via the electronic interface and store in the computer-readable memory, a digital image comprising a plurality of pixels, each pixel having a value in a first three-dimensional colour space;
      (ii) receive a mapping of values in a subset of the first colour space, the mapping specifying a modified colour value for each colour point in the subset, the mapping having been calculated by selecting a reference point in the subset and, for each colour point in the subset, mapping the colour point to the modified colour value offset from the reference point by a modified colour point vector calculated based on the colour point vector extending from the reference point to the colour point, the colour point vector having a direction and a magnitude;
      (iii) apply the mapping to the pixel values in the digital image falling in the subset to produce an enhanced image.

2. The image enhancement system of claim 1, wherein the modified colour point vector for each colour point in the subset has a direction equal to the direction of the colour point vector of the colour point, and a magnitude greater than the magnitude of the colour point vector.

3. The image enhancement system of claim 2, wherein the modified colour point vector is calculated by adding to the colour point vector a vector in the direction of the colour point vector having a magnitude equal to a constant with a value greater than zero.

4. The image enhancement system of claim 2, wherein the modified colour point vector is calculated by adding to the colour point vector a vector in the direction of the colour point vector having a magnitude equal to a contrast enhancement value that is a non-negative monotonically decreasing function of the magnitude of the colour point vector.

5. The image enhancement system of claim 1, wherein the subset of the first colour space is convex and the reference point is selected to be the geometric centre of the subset.

6. The image enhancement system of claim 5, wherein the first colour space is the RGB colour space, and the subset of the first colour space is a cuboid subset of the RGB colour space.

7. The image enhancement system of claim 5, wherein the subset of the first colour space is the subset of the first colour space corresponding to a subset of a second color space specified by upper and lower bounds of each of the three dimensions in the second colour space.

8. The image enhancement system of claim 7, wherein the first colour space is the RGB colour space and the second colour space in the HSV colour space.

9. The image enhancement system of claim 7, further comprising a display device for displaying images to a user, and a user input device for receiving input from a user, and wherein the user specifies the upper and lower bounds via the user interface, and the computer processor is further configured to receive the specification of the upper and lower bounds from the user interface, and display to the user on the display device the enhanced image.

10. The image enhancement system of claim 7, wherein the computer processor is further configured to automatically determine the upper and lower bounds by analysis of a specified portion of the digital image.

11. The image enhancement system of claim 1, wherein the computer processor is further configured to repeatedly enhance image frames of a video stream provided by an imaging system in real-time and display the sequence of enhanced images on a display device.

12. The image enhancement system of claim 1, wherein the mapping is implemented using a three dimensional look-up table (LUT) that is indexed by the pixel values in the subset of the first colour space, and for each of the pixel values specifies a modified pixel value.

13. A method of enhancing a digital image performed by a computer processor, the method comprising the steps of:
   (a) receiving a digital image comprising a plurality of pixels, each pixel having a value in a first three-dimensional colour space;
   (b) receiving a mapping of values in a subset of the first colour space, the mapping specifying a modified colour value for each colour point in the subset, the mapping having been calculated by selecting a reference point in the subset and, for each colour point in the subset, mapping the colour point to the modified colour value offset from the reference point by a modified colour point vector calculated based on the colour point vector extending from the reference point to the colour point, the colour point vector having a direction and a magnitude;
   (c) applying the mapping to the pixel values in the digital image falling in the subset to produce an enhanced image.

14. The method of claim 13, wherein, for each colour point in the subset, the modified colour point vector has a direction equal to the direction of the colour point vector of the colour point, and a magnitude greater than the magnitude of the colour point vector.

15. The method of claim 13, further comprising a step of calculating the mapping of values in the subset of the first colour space by the steps of:
   (a) selecting the reference point in the subset; and
   (b) for each colour point in the subset of the first colour space:
      (i) calculating a colour point vector extending from the reference point to the colour point, the colour point vector having a direction and a magnitude;
      (ii) calculating a modified colour point vector having a direction equal to the direction of the colour point vector, and a magnitude greater than the magnitude of the colour point vector; and
      (iii) mapping the colour point to the modified colour value offset from the reference point by the modified colour point vector.

16. The method of claim 15, wherein the subset of the first colour space is convex and the reference point is selected to be the geometric centre of the subset.

17. The method of claim 16, wherein the first colour space is the RGB colour space, and the subset of the first colour space is specified by specifying upper and lower bounds in each of the three dimensions in a second colour space.

18. The method of claim 17, wherein the second colour space is the HSV colour space so that the upper and lower bounds define a subset of the HSV colour space corresponding to a cuboid subset of the RGB colour space.

19. The method of claim 17, further comprising a step of providing a user interface to a user to permit the user to specify the upper and lower bounds, and displaying to the user the digital image showing only the pixels with values in the subset of the HSV colour space defined by the upper and lower bounds.

20. The method of claim 13, wherein the mapping is implemented using a three dimensional look-up table (LUT) that is indexed by the pixel values in the subset of the first colour space, and for each of the pixel values specifies a modified pixel value.

\* \* \* \* \*